United States Patent
Zaragoza Doerwald et al.

(10) Patent No.: US 10,882,816 B2
(45) Date of Patent: Jan. 5, 2021

(54) METHOD FOR THE PREPARATION OF 4-(HEPTAFLUORO-2-PROPYL) ANILINES

(71) Applicant: Lonza Ltd, Visp (CH)

(72) Inventors: Florencio Zaragoza Doerwald, Visp (CH); Daniel Zollinger, Sierre (CH)

(73) Assignee: Lonza Ltd, Visp (CH)

( * ) Notice: Subject to any disclaimer, the term of this patent is extended or adjusted under 35 U.S.C. 154(b) by 0 days.

(21) Appl. No.: 16/634,923

(22) PCT Filed: Aug. 7, 2018

(86) PCT No.: PCT/EP2018/071312
§ 371 (c)(1),
(2) Date: Jan. 29, 2020

(87) PCT Pub. No.: WO2019/030187
PCT Pub. Date: Feb. 14, 2019

(65) Prior Publication Data
US 2020/0262781 A1    Aug. 20, 2020

Related U.S. Application Data

(60) Provisional application No. 62/543,002, filed on Aug. 9, 2017.

(30) Foreign Application Priority Data

Aug. 9, 2017   (EP) .................................... 17020348
Dec. 15, 2017  (EP) .................................... 17207663
Mar. 7, 2018   (EP) .................................... 18160380

(51) Int. Cl.
*C07C 209/68* (2006.01)
*C07C 211/52* (2006.01)

(52) U.S. Cl.
CPC .......... *C07C 209/68* (2013.01); *C07C 211/52* (2013.01)

(58) Field of Classification Search
None
See application file for complete search history.

(56) References Cited

FOREIGN PATENT DOCUMENTS

JP   2003335735   11/2003

OTHER PUBLICATIONS

English Machine Translation of Kodama et al. (JP 2003335735) pub date 2003 (Year: 2003).*
International Search Report for PCT/EP2018/071312 dated Sep. 14, 2018, 17 pages.

* cited by examiner

*Primary Examiner* — Sudhakar Katakam
*Assistant Examiner* — Jennifer C Sawyer
(74) *Attorney, Agent, or Firm* — Dority & Manning, P.A.

(57) ABSTRACT

The invention discloses a method for the preparation of substituted 4-(heptafluoro-2-propyl) anilines by reaction of 2-bromoheptafluoropropane with anilines in the presence of sodium dithionite, in a solvent and in the presence of a catalyst.

5 Claims, No Drawings

METHOD FOR THE PREPARATION OF 4-(HEPTAFLUORO-2-PROPYL) ANILINES

CROSS REFERENCE TO RELATED APPLICATIONS

This application is the U.S. National Stage entry of International Application Number PCT/EP2018/071312 filed under the Patent Cooperation Treaty having a filing date of Aug. 7, 2018, which claims priority to European Patent Application No. 17020348.3 having a filing date of Aug. 9, 2017, European Patent Application No. 17207663.0 having a filing date of Dec. 15, 2017, European Patent Application No. 18160380.4 having a filing date of Mar. 7, 2018, and U.S. Patent App. No. 62/543,002 having a filing date of Aug. 9, 2017, which are incorporated herein by reference.

The invention discloses a method for the preparation of substituted 4-(heptafluoro-2-propyl) anilines by reaction of 2-bromoheptafluoropropane with anilines in the presence of sodium dithionite, in a solvent and in the presence of a catalyst.

BACKGROUND OF THE INVENTION

Substituted 4-(heptafluoro-2-propyl) anilines are important intermediates for the preparation of agrochemicals, for example such as Broflanilid with CAS 1207727-04-5.

U.S. Pat. No. 4,731,450 describes the perfluoro alkylation of aniline with perfluoroalkyl bromide in a polar aprotic solvent in the presence of zinc and sulfur dioxide. The prominent solvent in the examples is DMF.

JP 2003 335735 A discloses a process for producing perfluoroisopropylanilines by a reaction of perfluoroisopropyl bromide with an aniline in the presence of a reaction initiator and a base. The examples disclose only reaction mixtures which have two separate liquid phases, an aqueous phase and a phase formed by an organic solvent.

The yield in case of 2-toluidine being the substrate is 32% according to example 2.

The use of DMF as solvent for this type of reaction is problematic, because N-methyl amides are readily oxidized to derivatives of formaldehyde, which can react with the anilines, and which are difficult to remove from the product.

Thus, there is a need for a method for the alkylation of anilines with 2-bromoheptafluoropropane and which does not require the use of DMF as solvent and which does not require the use of zinc.

It was found that substituted anilines can be alkylated with 2-bromoheptafluoropropane in an organic solvent in the presence of a reducing agent such as sodium dithionite and in the presence of an acidic substance, without the mandatory need of adding water or other cosolvents, without the mandatory need to carry out the reaction in a system containing two liquid phases, without the need of any phase transfer catalysts and without the use of zinc or DMF or sulfur dioxide.

The reaction mixture of instant invention has only one liquid phase, and with 2-toluidine as substrate in Example 7 a yield of 52% was obtained, whereas Example 2 of JP 2003 335735 A shows only a yield of 32%. It was not expected in view of JP 2003 335735 A, which discloses a bi-phasic reaction mixture with two liquid phases, that the yield would improve when carrying out the reaction in a reaction mixture having only one liquid phase, and where in addition the sodium dithionite would not be soluble in the one liquid phase, when no water is added to the reaction mixture.

Furthermore the reaction is done in the presence of an acidic substance, whereas JP 2003 335735 A requires the presence of a base.

Also Comparative Example 3 shows a low yield, it is an example with a procedure in analogy to Example 2 of JP 2003 335735 A using the system with two liquid phases and a phase-transfer catalyst, but with 2-trifluoromethylaniline as substrate instead of 2-toluidine. It showed a yield of only 9%, whereas the Example 3 and the Example 6 of instant invention show a yield of 73% and of 78% respectively.

Herein the following abbreviations and synonyms are used, if not otherwise stated:
DMF dimethyl formamide
sodium hydrogen sulfate sodium bisulfate
potassium hydrogen sulfate potassium bisulfate
sodium dithionite $Na_2S_2O_4$

SUMMARY OF THE INVENTION

Subject of the invention is a method for the preparation of compound of formula (I);

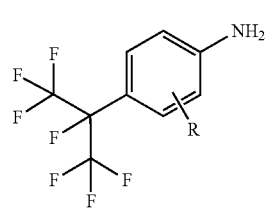

the method comprises a reaction REAC1, wherein compound of formula (II)

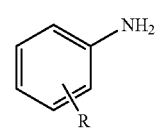

is reacted with 2-bromoheptafluoropropane in the presence of sodium dithionite, in a solvent SOLV1 and in the presence of a catalyst CAT1;
wherein the reaction mixture of REAC1 has only one liquid phase;
R is $CF_3$ or methyl;
SOLV1 is selected from the group consisting of methyl acetate, ethyl acetate, butyl acetate, propyl acetate, isopropyl acetate, tert-butylacetate, dimethyl carbonate, diethyl carbonate, acetone, 2-butanone, ethylene glycol, acetonitrile, propionitrile, valeronitrile, 1,4-dioxane, tetrahydrofuran, 2-methyl tetrahydrofuran, 1,2-dimethoxyethane, methyl tert-butyl ether, sulfolane, and mixtures thereof;
CAT1 is selected from the group consisting of formic acid, acetic acid, propionic acid, benzoic acid, sulfuric acid, hydrochloric acid, sodium hydrogen sulfate, potassium hydrogen sulfate, tetramethylammonium hydrogen sulfate, tetrabutylammonium hydrogen sulfate, $NaH_2PO_4$, $Na_2HPO_4$, $KH_2PO_4$, $K_2HPO_4$, $Bu_4NH_2PO_4$, sulfamic acid, pyridinium hydrochloride, methane sulfonic acid, toluene sulfonic acid, and mixtures thereof.

DETAILED DESCRIPTION OF THE INVENTION

Preferably, compound of formula (I) is compound of formula (I-1) or compound of formula (I-2);

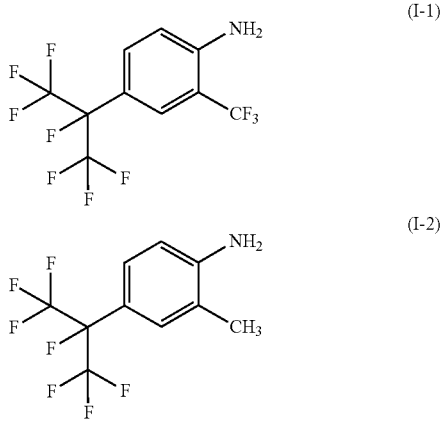

more preferably, compound of formula (I) is compound of formula (I-1).

Preferably, compound of formula (II) is compound of formula (II-1) or compound of formula (II-2);

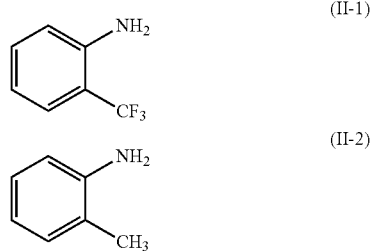

more preferably, compound of formula (II) is compound of formula (II-1).

Preferably, SOLV1 is selected from the group consisting of ethyl acetate, tert-butyl acetate, dimethyl carbonate, acetone, 2-butanone, ethylene glycol, acetonitrile, propionitrile, valeronitrile, 1,4-dioxane, methyl tert-butyl ether, sulfolane, and mixtures thereof;

more preferably, SOLV1 is selected from the group consisting of ethylene glycol, acetonitrile, propionitrile, valeronitrile, and mixtures thereof;

even more preferably, SOLV1 is acetonitrile.

Preferably, the weight of SOLV1 in REAC1 is from 0.1 to 100 times, more preferably from 0.2 to 50 times, even more preferably from 0.5 to 30 times, especially from 0.75 to 20 times, more especially from 0.75 to 10 times, of the weight of compound of formula (II).

The liquid phase of the reaction mixture in REAC1 has only one phase, SOLV1 is chosen respectively. The reaction mixture of REAC1 is not a biphasic mixture with two liquid phases.

Preferably, no water is used in REAC1, that is no water is added to the reaction mixture of REAC1, REAC1 is done without the addition of water.

REAC1 can be done in the presence of water. When REAC1 is done in the presence of water, then preferably REAC1 is done in the presence of such amounts of water that no second liquid phase forms.

Preferably, REAC1 is done in the absence of a phase transfer catalyst; REAC1 is preferably done without the presence of a phase transfer catalyst.

Preferably, none of sulfur dioxide, DMF, dimethyl sulfoxide, hexamethylphosphoramide, dimethylacetamide, N-methylpyrrolidone and any pyridine is added to REAC1; REAC1 is preferably done without the presence of these substances.

Preferably, no metal selected from the group consisting of zinc, aluminum, manganese, cadmium, iron, magnesium, tin, nickel and cobalt is added to REAC1; REAC1 is preferably done in the absence of these metals.

Preferably, CAT1 is selected from the group consisting of acetic acid, propionic acid, sulfuric acid, hydrochloric acid, sodium hydrogen sulfate, potassium hydrogen sulfate, tetrabutylammonium hydrogen sulfate, $NaH_2PO_4$, $Na_2HPO_4$, $KH_2PO_4$, $K_2HPO_4$, $Bu_4NH_2PO_4$, pyridinium hydrochloride, toluene sulfonic acid, and mixtures thereof;

more preferably, CAT1 is selected from the group consisting of acetic acid, sulfuric acid, hydrochloric acid, sodium hydrogen sulfate, potassium hydrogen sulfate, tetrabutylammonium hydrogen sulfate, $NaH_2PO_4$, $Na_2HPO_4$, $Bu_4NH_2PO_4$, pyridinium hydrochloride, toluene sulfonic acid, and mixtures thereof;

even more preferably, CAT1 is selected from the group consisting of acetic acid, sulfuric acid, sodium hydrogen sulfate, tetrabutylammonium hydrogen sulfate, $NaH_2PO_4$, $Na_2HPO_4$, $Bu_4NH_2PO_4$, toluene sulfonic acid, and mixtures thereof;

especially, CAT1 is selected from the group consisting of acetic acid, sulfuric acid, sodium hydrogen sulfate, tetrabutylammonium hydrogen sulfate, and mixtures thereof.

Preferably, the molar amount of CAT1 in REAC1 is from 0.01 to 20 times, more preferably from 0.05 to 10 times, even more preferably from 0.05 to 5 times, especially from 0.05 to 2 times, more especially from 0.05 to 1 times, even more especially from 0.05 to 0.75 times, in particular from 0.05 to 0.5 times, of the molar amount of compound of formula (II).

Preferably, the molar amount of sodium dithionite in REAC1 is from 0.01 to 5 times, more preferably from 0.02 to 3 times, even more preferably from 0.03 to 2 times, especially from 0.075 to 2 times, more especially from 0.1 to 2 times, of the molar amount of compound of formula (II).

In another preferred embodiment, the molar amount of sodium dithionite in REAC1 is from 0.1 to 5 times, more preferably from 0.2 to 3 times, even more preferably from 0.3 to 2 times, especially from 0.75 to 2 times, more especially from 1 to 2 times, of the molar amount of compound of formula (II).

The total quantity of sodium dithionite, that is used in REAC1, can be added portion wise during REAC1, this portion wise addition can be extended over the whole reaction time. Preferably, the portions have equal size and are added in equal intervals of time.

Preferably, the molar amount of 2-bromoheptafluoropropane in REAC1 is from 0.01 to 50 times, more preferably from 0.05 to 20 times, even more preferably from 0.1 to 10 times, of the molar amount of compound of formula (II).

When 2-bromoheptafluoropropane is used in sub stoichiometric amounts, that is in an amount of less than one equivalent, relative to compound of formula (II), then REAC1 provides for a mixture of compound of formula (I) and compound of formula (II);

said mixture of compound of formula (I) and compound of formula (II) can be separated using standard methods, such as distillation, preferably under reduced pressure;

the separated compound of formula (II) can then be fed again into REAC1; this embodiment is for example suited for a continuous process set up.

Preferably, when 2-bromoheptafluoropropane is used in sub stoichiometric amounts relative to compound of formula (II), then also sodium dithionite is used in sub stoichiometric amounts, that is in an amount of less than one equivalent, relative to compound of formula (II) is used in REAC1.

In a continuous process set up, sodium dithionite can also be added continuously to REAC1.

Preferably, in a continuous process set up CAT1 and SOLV1 are fed continuously into REAC1, 2-bromoheptafluoropropane and sodium dithionite are also fed, preferably in sub stoichiometric amounts, into REAC1, the obtained mixture of compound of formula (I) and compound of formula (II) from REAC1 as well as SOLV1 are continuously separated, and the thus separated compound of formula (II) and SOLV1 are fed back into REAC1.

Preferably, the reaction temperature of REAC1 is from −70 to 180° C., more preferably from −30 to 130° C., even more preferably from 0 to 100° C., especially from 20 to 80° C., more especially from 40 to 80° C., even more especially from 50 to 80° C.

Preferably, the reaction time of REAC1 is from 0.1 to 200 h, more preferably from 0.5 to 100 h, even more preferably from 1 to 50 h, especially from 2 to 24 h, more especially from 3 to 24 h.

Preferably, REAC1 is done under atmospheric pressure or under elevated pressure, such as from atmospheric pressure to 100 bar.

Elevated pressure can be applied by used of an inert gas such as argon, or by charging 2-bromoheptafluoropropane with a respective pressure.

After REAC1, compound of formula (I) can be isolated by standard methods such as evaporation of volatile components, distillation, preferably under reduced pressure, extraction, washing, drying, concentration, crystallization, chromatography and any combination thereof, which are known per se to the person skilled in the art.

EXAMPLES

Raw Materials:
Sodium dithionite content 85% by weight, technical grade, available from Sigma Aldrich Example 1

4-(Heptafluoro-2-propyl)-2-trifluoro methyl aniline; Sulfuric acid as CAT1

A mixture of 2-trifluoro methyl aniline (0.252 ml, 2.00 mmol), acetonitrile (1.3 ml), sulfuric acid (0.020 ml, 0.38 mmol), and sodium dithionite (492 mg, 2.40 mmol) was placed under an atmosphere of 2-bromoheptafluoropropane at atmospheric pressure and was stirred at 65° C. for 4.5 h. The reaction mixture was diluted with brine (8 ml), made basic by addition of solid $Na_2CO_3$ (ca. 0.5 g), and extracted (6 ml AcOEt). Concentration of a sample of the organic phase and analysis of the residue by $^1H$ NMR indicated, that a mixture of 2-trifluoromethylaniline and 4-(heptafluoro-2-propyl)-2-trifluoromethylaniline in a molar ratio of 0.32 to 1.00 had been formed.

Example 2

4-(Heptafluoro-2-propyl)-2-trifluoromethylaniline; Acetic acid as CAT1

A mixture of 2-trifluoromethylaniline (0.252 ml, 2.00 mmol), acetonitrile (0.55 ml), acetic acid (0.023 ml, 0.40 mmol), and sodium dithionite (492 mg, 2.40 mmol) was placed under an atmosphere of 2-bromoheptafluoropropane at atmospheric pressure and was stirred at 65° C. for 16 h. The mixture was diluted with brine (8 ml), made basic by addition of solid $Na_2CO_3$ (ca. 0.5 g), and extracted (6 ml AcOEt). Concentration of a sample of the organic phase and analysis of the residue by $^1H$ NMR indicated, that a mixture of 2-trifluoromethylaniline and 4-(heptafluoro-2-propyl)-2-trifluoromethylaniline in a molar ratio of 0.09 to 1.00 had been formed.

Example 3

4-(Heptafluoro-2-propyl)-2-trifluoromethylaniline; Sodium bisulfate as CAT1, Yield with Respect to 2-trifluoromethylaniline Used A mixture of 2-trifluoromethylaniline (0.252 ml, 2.00 mmol), acetonitrile (0.55 ml), $NaHSO_4$ (24 mg, 0.20 mmol), and sodium dithionite (492 mg, 2.40 mmol) was placed under an atmosphere of 2-bromoheptafluoropropane at atmospheric pressure and was stirred at 65° C. for 16 h. The mixture was diluted with brine (8 ml), made basic by addition of solid $Na_2CO_3$ (ca. 0.5 g), and extracted (6 ml AcOEt). Concentration of a sample of the organic phase and analysis of the residue by $^1H$ NMR indicated, that a mixture of 2-trifluoromethylaniline and 4-(heptafluoro-2-propyl)-2-trifluoromethylaniline in a molar ratio of 0.02 to 1.00 had been formed.

$^1H$ NMR (DMSO, 400 MHz) delta=7.51 (d, J=8 Hz, 1H), 7.48 (s, br, 1H), 7.08 (d, J=8 Hz, 1H), 6.36 (s, br, 2H).

In a repetition of this example, the yield of 4-(heptafluoro-2-propyl)-2-trifluoromethylaniline, as determined by $^1H$ NMR with an internal standard ($iBu_3PO_4$), was 73% with respect to the 2-trifluoromethylaniline used.

Example 4

4-(Heptafluoro-2-propyl)-2-trifluoromethylaniline; $Bu_4NHSO_4$ as CAT1

A mixture of 2-trifluoromethylaniline (0.252 ml, 2.00 mmol), acetonitrile (0.40 ml), $Bu_4NHSO_4$ (81 mg, 0.24 mmol), and sodium dithionite (492 mg, 2.40 mmol) was placed under an atmosphere of 2-bromoheptafluoropropane at atmospheric pressure and was stirred at 65° C. for 17 h. The mixture was diluted with brine (8 ml), made basic by addition of solid $Na_2CO_3$ (ca. 0.5 g), and extracted (6 ml AcOEt). Concentration of a sample of the organic phase and analysis of the residue by $^1H$ NMR indicated, that a mixture of 2-trifluoromethylaniline and 4-(heptafluoro-2-propyl)-2-trifluoromethylaniline in a molar ratio of 0.03 to 1.00 had been formed.

Example 5

4-(Heptafluoro-2-propyl)-2-trifluoromethylaniline; Sodium Bisulfate as CAT1; Addition of Dithionite Portion Wise A mixture of 2-trifluoromethylaniline (8.05 g, 50.0 mmol), acetonitrile (13 ml), sodium bisulfate (637 mg, 5.31 mmol) was placed under an atmosphere of 2-bromoheptafluoropropane at atmospheric pressure and heated to 65° C. Within 2 h and 40 min sodium dithionite (12.4 g, 60.5 mmol) was added in five equally sized portions while stirring at 65° C., a portion was added every 25 min. When the addition was finished, stirring at 65° C. was continued for 17 h. A sample of the reaction mixture was diluted with aqueous solution of $Na_2CO_3$ (ca. 0.5 g of $Na_2CO_3$ in ca. 3 ml water) the resulting dilution was extracted with AcOEt, and the organic extract was concentrated under reduced pressure. Analysis of the residue by $^1H$ NMR indicated that a mixture of 2-trifluoromethylaniline and 4-(heptafluoro-2-propyl)-2-trifluoromethylaniline in a molar ratio of 16:84 had been formed.

Comparative Example 1

Attempt of Perfluoro Alkylation without CAT1

A mixture of 2-trifluoromethylaniline (0.252 ml, 2.00 mmol), acetonitrile (1.0 ml), and sodium dithionite (615 mg, 3.0 mmol) was placed under an atmosphere of 2-bromoheptafluoropropane at atmospheric pressure and was stirred at 65° C. for 5 h. The mixture was diluted with brine (8 ml), made basic by addition of solid $Na_2CO_3$ (ca. 0.5 g), and extracted (6 ml AcOEt). Concentration of a sample of the organic phase and analysis of the residue by $^1H$ NMR indicated that no alkylation of the 2-trifluoromethylaniline had occurred.

Comparative Example 2

Attempt of Perfluoro Alkylation in the Presence of $K_2CO_3$

A mixture of 2-trifluoromethylaniline (0.252 ml, 2.00 mmol), acetonitrile (1.0 ml), potassium carbonate (335 mg, 2.42 mmol), and sodium dithionite (492 mg, 2.40 mmol) was placed under an atmosphere of 2-bromoheptafluoropropane at atmospheric pressure and was stirred at 65° C. for 3.5 h. The mixture was diluted with brine (8 ml) and extracted (6 ml AcOEt). Concentration of a sample of the organic phase and analysis of the residue by $^1H$ NMR indicated, that a mixture of 2-trifluoromethylaniline and 4-(heptafluoro-2-propyl)-2-trifluoromethylaniline in a molar ratio of 1.00:0.03 had been formed.

Example 6

Isolation and Yield with Respect to heptafluoro-2-bromopropane Used

Into an autoclave were added 2-trifluoromethylaniline (19.2 ml, 151 mmol), acetonitrile (122 ml), $NaHSO_4$ (1.91 g, 15.9 mmol), and sodium dithionite (85%, 18.7 g, 90.4 mmol). To this mixture heptafluoro-2-bromopropane (10.0 ml, 75.3 mmol) was added, and the mixture was stirred at 65° C. for 17 h. Analysis of a sample by 1H NMR indicated that 59 mmol of 4-(heptafluoro-2-propyl)-2-trifluoromethylaniline had been formed.

The mixture was diluted with water (150 ml), basified with solid $NaHCO_3$, phases were separated, the aqueous phase was extracted with ethyl acetate (once with 100 ml and once with 50 ml), the combined organic phases were washed once with brine (100 ml), dried ($MgSO_4$), and concentrated under reduced pressure to yield 43.3 g of an oil. Quantification by $^1H$ NMR with internal standard (sulfolane) indicated that 59.0 mmol of 4-(heptafluoro-2-propyl)-2-trifluoromethylaniline had been formed (78% yield with respect to heptafluoro-2-bromopropane used).

Example 7

4-(Heptafluoro-2-propyl)-2-methylaniline

Into an autoclave were added 2-methylaniline (25.6 ml, 240 mmol), acetonitrile (64 ml), $NaHSO_4$ (2.93 g, 24.4 mmol), and sodium dithionite (85%, 56.8 g, 277 mmol). The mixture was heated to 67° C. and heptafluoro-2-bromopropane (46 ml, 347 mmol) was added within 3 h. The mixture was stirred at 67° C. for 15 h.

The mixture was diluted with water (250 ml), basified with solid $NaHCO_3$, phases were separated, the aqueous phase was extracted with ethyl acetate (once with 100 ml and once with 50 ml), the combined organic phases were washed once with brine (100 ml), dried ($MgSO_4$), and concentrated under reduced pressure to yield 76.5 g of an oil. Quantification by $^1H$ NMR with internal standard (sulfolane) indicated that 125 mmol of 4-(heptafluoro-2-propyl)-2-methylaniline had been formed (52% yield with respect to 2-methylaniline used).

Comparative Example 3

4-(Heptafluoro-2-propyl)-2-trifluoromethylaniline; Procedure in Analogy to Example 2 of JP 2003 335735 A (System with Two Liquid Phases and Phase-Transfer Catalyst)

The procedure of Example 2 of JP 2003 335735 A was repeated with the differences that
  2-trifluoromethylaniline was used instead of 2-toluidine,
  a 250 ml autoclave was used instead of a 100 ml autoclave, which required also an upscaling by a factor of 1.4 in order to ensure stirring of the reaction mixture in the 250 ml autoclave, and
  heptafluoro-2-bromopropane was added as last addition since it had to be added under pressure after closing of the autoclave:
  Into an 250 ml autoclave were added water (27.8 ml), methyl tert-butyl ether (27.8 ml), sodium dithionite (85%, 3.69 g, 18.0 mmol), $NaHCO_3$ (1.53 g, 18.2 mmol), 2-trifluoromethylaniline (1.91 ml, 15.2 mmol), and tetrabutylammonium hydrogensulfate (0.58 g, 1.71 mmol). Then, while stirring at 20° C., heptafluoro-2-bromopropane (3.68 ml, 27.7 mmol) was added, and stirring was continued for 8 h.

Phases were separated, the aqueous phase was extracted with AcOEt (25 ml), the combined organic phases were washed with 2N aqueous HCl (50 ml), with 5% aqueous $Na_2CO_3$ solution (50 ml), with brine (50 ml), and were dried ($MgSO_4$). Filtration and concentration yielded 5.75 g of an oil. Analysis by $^1H$ NMR with sulfolane as internal standard indicated, that 1.40 mmol (9%) of 4-(heptafluoro-2-propyl)-2-trifluoromethylaniline had been formed.

The skilled person has no reason to suspect that the additional differences between this Comparative Example 3 on the one side, and the Example 2 of the JP 2003 335735 A on the other side, which were introduced into the procedure of Example 2 of JP 2003 335735 A in addition to the change from 2-toluidine to 2-trifluormethylaniline, might be responsible for the low yield in comparison to the procedure of instant invention. The skilled person will rather expect that the principal differences between the procedure of instant invention and the procedure of JP 2003 335735 A, namely the use of a reaction mixture with only one liquid phase (instant invention) instead of a reaction mixture with two liquid phases together with the use of a phase transfer catalyst (Example 2 of JP 2003 335735 A), is the reason for the better performance of the procedure of the instant invention.

The invention claimed is:

1. A method for the preparation of compound of formula (I);

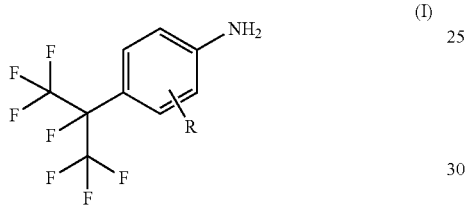

the method comprises a reaction REAC1, wherein compound of formula (II)

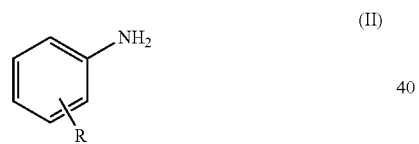

is reacted with 2-bromoheptafluoropropane in the presence of sodium dithionite, in a solvent SOLV1 and in the presence of a catalyst CAT1;
wherein the reaction mixture of REAC1 has only one liquid phase;
R is $CF_3$ or methyl;
SOLV1 is selected from the group consisting of methyl acetate, ethyl acetate, butyl acetate, propyl acetate, isopropyl acetate, tert-butylacetate, dimethyl carbonate, diethyl carbonate, acetone, 2-butanone, ethylene glycol, acetonitrile, propionitrile, valeronitrile, 1,4-dioxane, tetrahydrofuran, 2-methyl tetrahydrofuran, 1,2-dimethoxyethane, methyl tert-butyl ether, sulfolane, and mixtures thereof;
CAT1 is selected from the group consisting of formic acid, acetic acid, propionic acid, benzoic acid, sulfuric acid, hydrochloric acid, sodium hydrogen sulfate, potassium hydrogen sulfate, tetramethylammonium hydrogen sulfate, tetrabutylammonium hydrogen sulfate, $NaH_2PO_4$, $Na_2HPO_4$, $KH_2PO_4$, $K_2HPO_4$, $Bu_4NH_2PO_4$, sulfamic acid, pyridinium hydrochloride, methane sulfonic acid, toluene sulfonic acid, and mixtures thereof.

2. The method according to claim 1, wherein compound of formula (I) is compound of formula (I-1) or compound of formula (I-2).

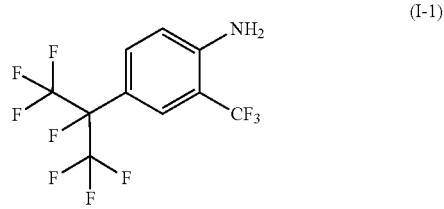

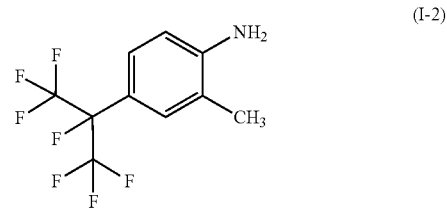

3. The method according to claim 1, wherein
compound of formula (II) is compound of formula (II-1) or compound of formula (II-2).

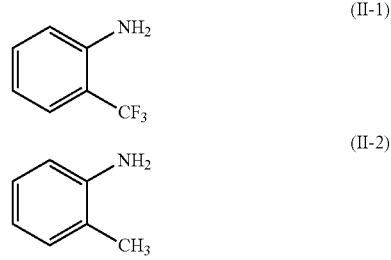

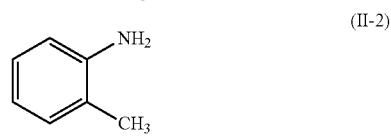

4. The method according to claim 1, wherein
SOLV1 is selected from the group consisting of ethyl acetate, tert-butyl acetate, dimethyl carbonate, acetone, 2-butanone, ethylene glycol, acetonitrile, propionitrile, valeronitrile, 1,4-dioxane, methyl tert-butyl ether, sulfolane, and mixtures thereof.

5. The method according to claim 1, wherein
CAT1 is selected from the group consisting of acetic acid, propionic acid, sulfuric acid, hydrochloric acid, sodium hydrogen sulfate, potassium hydrogen sulfate, tetrabutylammonium hydrogen sulfate, $NaH_2PO_4$, $Na_2HPO_4$, $KH_2PO_4$, $K_2HPO_4$, $Bu_4NH_2PO_4$, pyridinium hydrochloride, toluene sulfonic acid, and mixtures thereof.

* * * * *